US00PP18942P2

(12) United States Plant Patent
de Boer

(10) Patent No.: US PP18,942 P2
(45) Date of Patent: Jun. 17, 2008

(54) *ERYNGIUM* PLANT NAMED 'PARADISE JACKPOT'

(50) Latin Name: *Eryngium planum*
Varietal Denomination: Paradise Jackpot

(76) Inventor: Huibert Anne de Boer, Collegiantenstraat 90, 2231 HM Rijnsburg (NL)

( * ) Notice: Subject to any disclaimer, the term of this patent is extended or adjusted under 35 U.S.C. 154(b) by 0 days.

(21) Appl. No.: 11/725,795

(22) Filed: Mar. 20, 2007

(51) Int. Cl.
*A01H 5/00* (2006.01)

(52) U.S. Cl. ..... Plt./361

(58) Field of Classification Search ..... Plt./361
See application file for complete search history.

(56) References Cited

PUBLICATIONS

UPOVROM search for cultivar Paradise Jackpot PBR 20041821 p. 1.*

* cited by examiner

*Primary Examiner*—Annette H Para
(74) *Attorney, Agent, or Firm*—C. A. Whealy

(57) ABSTRACT

A new and distinct cultivar of *Eryngium* plant named 'Paradise Jackpot', characterized by its upright and inverted narrow triangular plant habit; moderately vigorous growth habit; freely branching habit; and compound flower heads with blue-colored flowers.

2 Drawing Sheets

Botanical designation: *Eryngium planum.*
Cultivar denomination: 'Paradise Jackpot'.

BACKGROUND OF THE INVENTION

The present invention relates to a new and distinct cultivar of *Eryngium* plant, botanically known as *Eryngium planum,* and hereinafter referred to by the name 'Paradise Jackpot'.

The new *Eryngium* was discovered by the Inventor in a controlled environment in Rijnsburg, The Netherlands, in July, 2001, as a naturally-occurring whole plant mutation of an unnamed seedling selection of *Eryngium planum,* not patented. The new *Eryngium* was observed as a single plant from within a population of plants of the parent selection. The selection of this plant was based on its unique inflorescence form.

Asexual reproduction of the new *Eryngium* by cuttings in a controlled environment in Rijnsburg, The Netherlands since March, 2002, has shown that the unique features of this new *Eryngium* are stable and reproduced true to type in successive generations.

SUMMARY OF THE INVENTION

The cultivar Paradise Jackpot has not been observed under all possible environmental conditions. The phenotype may vary somewhat with variations in environment such as temperature and light intensity, without, however, any variance in genotype.

The following traits have been repeatedly observed and are determined to be the unique characteristics of 'Paradise Jackpot'. These characteristics in combination distinguish 'Paradise Jackpot' as a new and distinct cultivar of *Eryngium:*

1. Upright and inverted narrow triangular plant habit.
2. Moderately vigorous growth habit.
3. Freely branching habit.
4. Compound flower heads with blue-colored flowers.

Plants of the new *Eryngium* differ from plants of the parent selection primarily in inflorescence form as plants of the parent selection have simple (not compound) inflorescence heads.

Plants of the new *Eryngium* can also be compared to plants of the *Eryngium planum* cultivar Blue Dwarf, not patented. Plants of the new *Eryngium* differ from plants of the cultivar Blue Dwarf primarily in inflorescence form as plants of the cultivar Blue Dwarf have simple (not compound) inflorescence heads.

BRIEF DESCRIPTION OF THE PHOTOGRAPHS

The accompanying photographs illustrate the overall appearance of the new *Eryngium.* The photographs show the colors as true as it is reasonably possible to obtain in colored reproductions of this type. Colors in the photographs may differ slightly from the color values cited in the detailed botanical description which accurately describe the colors of the new *Eryngium.*

The photograph on the first sheet comprises a side perspective view of a typical flowering plant of 'Paradise Jackpot' grown in an outdoor nursery.

The photograph at the top of the second sheet is a close-up view of a typical flowering stem of 'Paradise Jackpot'.

The photograph at the bottom of the second sheet is a close-up view of a typical compound inflorescence of 'Paradise Jackpot'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown in Rijnsburg, The Netherlands during the late summer in an outdoor nursery and under conditions and practices which approximate those generally used in commercial *Eryngium* production. During the production of the plants, day temperatures ranged from 15° C. to 22° C. and night temperatures ranged from 6° C. to 13° C. Measurements and numerical values represent averages for typical flowering plants. Plants were about one year old when the photographs and description were taken.

Botanical classification: *Eryngium planum* cultivar Paradise Jackpot.

Parentage: Naturally-occurring whole plant mutation of an unnamed seedling selection of *Eryngium planum,* not patented.

Propagation:

*Type.*—By cuttings.

*Time to initiate roots.*—About 80 days at 12° C.

*Time to produce a rooted young plant.*—About six months at 18° C.

*Root description.*—Fibrous, fleshy and thick; white in color.

*Rooting habit.*—Freely branching; dense.

Plant description:

*Plant form/growth habit.*—Herbaceous perennial; upright and inverted narrow triangular plant habit; freely branching with about nine lateral branches developing per plant. Moderately vigorous growth habit.

*Plant height.*—About 64 cm.

*Plant diameter or spread.*—About 37 cm.

*Lateral branches.*—Length: About 13.6 cm. Diameter: About 3 mm. Aspect: Mostly upright to slightly outward. Strength: Strong. Texture: Smooth, glabrous. Color: Between 147C and 148B; tinged with 92B.

Foliage description:

*Arrangement.*—Alternate, simple; sessile.

*Length, upper leaves.*—About 3.6 cm.

*Length, lower leaves.*—About 7.6 cm.

*Width, upper leaves.*—About 4.4 cm.

*Width, lower leaves.*—About 6.4 cm.

*Shape, upper leaves.*—Palmately lobed.

*Shape, lower leaves.*—Ovate.

*Apex, upper leaves.*—Mucronate.

*Apex, lower leaves.*—Mucronulate.

*Base, upper and lower leaves.*—Hastate.

*Margin, upper leaves.*—Serrate.

*Margin, lower leaves.*—Crenate.

*Texture, upper and lower leaves, upper and lower surfaces.*—Smooth, glabrous; leathery.

*Venation pattern, upper and lower leaves.*—Pinnate.

*Color, upper and lower leaves.*—Developing foliage, upper surface: 137C. Developing foliage, lower surface: 138A. Fully expanded foliage, upper surface: 137B to 137C; venation, 145D. Fully expanded foliage, lower surface: 138A; venation, 138A.

Flower description:

*Flower arrangement and habit.*—Single rotate flowers arranged on unique compound flower heads; flowers sessile. Inflorescences arising from leaf axils. Freely flowering habit with usually about 600 flowers developing per inflorescence. Flowers persistent. Flowers face upright and outwardly. Flowers moderately fragrant; unpleasant.

*Natural flowering season.*—Plants of the new *Eryngium* initiate and develop flowers during the late summer and flower continuously from August through October in The Netherlands.

*Flower longevity.*—Flowers last about two weeks on the plant.

*Inflorescence height.*—About 12.8 cm.

*Inflorescence diameter.*—About 5.2 cm.

*Flower diameter.*—About 3 mm.

*Flower length (depth).*—About 5 mm.

*Flower bud.*—Shape: Obovate. Length: About 3 mm. Diameter: About 1.5 mm. Color: 145B.

*Petals.*—Arrangement: Five petals in a single whorl. Length: About 1.8 mm. Width: About 1 mm. Shape: Elliptic. Apex: Acute; recurved. Margin: Entire. Texture, upper and lower surfaces: Smooth, glabrous. Color: When opening, upper and lower surfaces: 97B to 97C. Fully opened, upper and lower surfaces: 96A; color becoming closer to 98C to 98D with development.

*Sepals.*—Arrangement: Five sepals in a single whorl. Length: About 3 mm. Width: About 1.5 mm. Shape: Ovate. Apex: Acute. Base: Cuneate. Margin: Entire. Texture, upper and lower surfaces: Smooth, glabrous. Color, immature, upper and lower surfaces: 145B. Color, mature, upper and lower surfaces: 144A to 144B.

*Inflorescence bracts.*—Arrangement: About twelve bracts in a single whorl subtending the flower head. Length: About 1.7 cm. Width: About 8 mm. Shape: Ovate. Apex: Apiculate. Base: Cuneate. Margin: Entire. Texture, upper and lower surfaces: Smooth, glabrous. Color, immature and mature, upper and lower surfaces: 137C.

*Peduncles.*—Length: About 7.7 cm. Diameter: About 2 mm. Angle: Main peduncle, erect; lateral peduncles, about 30° from vertical. Strength: Strong. Texture: Smooth, glabrous. Color: Between 147C and 148B; tinged with 96D.

*Reproductive organs.*—Stamens: Quantity/arrangement: About four per flower. Anther shape: Ovate. Anther length: About 1 mm. Anther color: N92B. Filament length: About 2.5 mm. Filament color: 97A. Pollen amount: Moderate. Pollen color: 156D. Pistils: Quantity: About two per flower. Pistil length: About 3 mm. Style length: About 2.8 mm. Style color: 95D to lighter than 95D. Stigma shape: Rounded. Stigma color: 95D to lighter than 95D. Ovary color: 144B to 144C. Fruits/seeds: Fruit and seed development have not been observed.

Disease/pest resistance: Plants of the new *Eryngium* have not been shown to be resistant to pathogens and pests common to *Eryngium.*

Garden performance: Plants of the new *Eryngium* have exhibited good tolerance to rain and wind, have been observed to tolerate temperatures from about −20° C. to about 35° C.

It is claimed:

1. A new and distinct *Eryngium* plant named 'Paradise Jackpot' as illustrated and described.

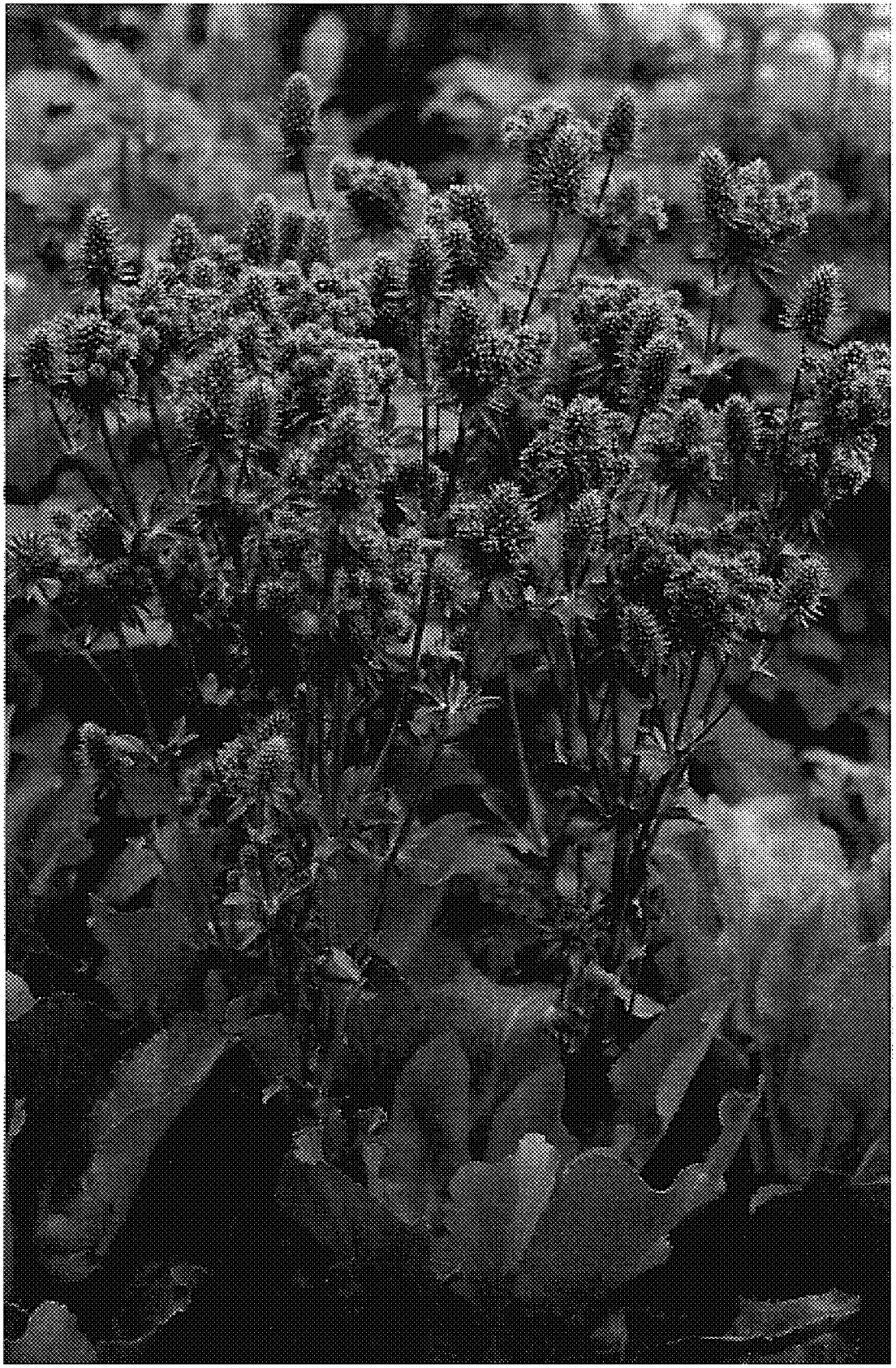

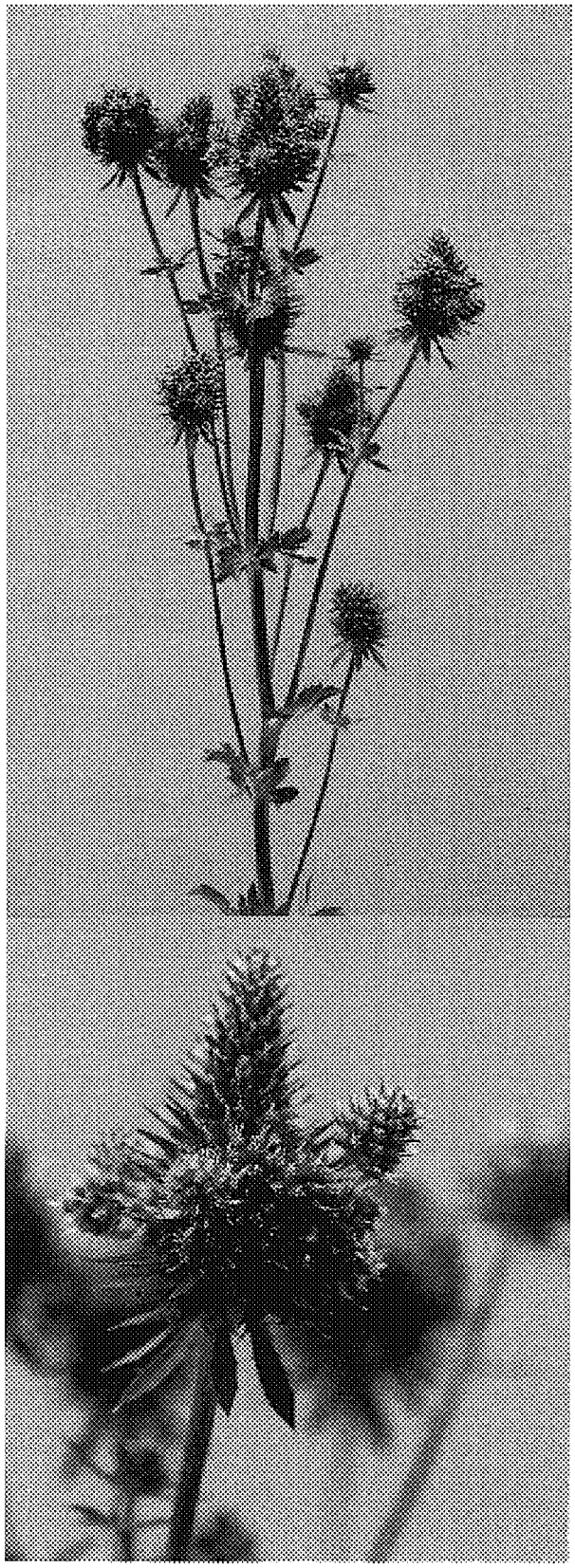

* * * * *